(12) United States Patent
Chen

(10) Patent No.: US 6,805,689 B2
(45) Date of Patent: Oct. 19, 2004

(54) SAFETY BLOOD COLLECTOR DEVICE

(76) Inventor: Wei Chen, 16942 Anna Green, Houston, TX (US) 77084

(*) Notice: Subject to any disclaimer, the term of this patent is extended or adjusted under 35 U.S.C. 154(b) by 186 days.

(21) Appl. No.: 10/003,447

(22) Filed: Oct. 23, 2001

(65) Prior Publication Data

US 2003/0078544 A1 Apr. 24, 2003

(51) Int. Cl.[7] .......................... A61M 5/32; A61M 1/00; A61F 13/15; A61B 5/00; B65D 81/00
(52) U.S. Cl. ...................... 604/198; 604/363; 604/540; 600/576; 600/577; 600/580
(58) Field of Search .................. 604/198, 199, 604/110, 192, 263, 197, 195, 162, 167, 187, 196, 232, 540; 128/919; 600/573–581

(56) References Cited

U.S. PATENT DOCUMENTS

| | | | |
|---|---|---|---|
| 2,376,436 A | 5/1945 | Lawshe ..................... 604/240 |
| 2,392,196 A | 1/1946 | Smith ......................... 604/235 |
| 3,706,306 A | 12/1972 | Berger et al. ............... 128/762 |
| 4,123,091 A | 10/1978 | Cosentino et al. .......... 604/240 |
| 4,641,663 A | 2/1987 | Juhn .......................... 128/765 |
| 4,653,511 A | 3/1987 | Goch .......................... 128/765 |
| 4,710,170 A | 12/1987 | Haber et al. ............... 604/240 |
| 4,731,059 A | 3/1988 | Wanderer et al. .......... 128/764 |
| 4,784,650 A | 11/1988 | Coburn ........................ 128/764 |
| 4,810,248 A * | 3/1989 | Masters et al. .............. 604/192 |
| 4,978,344 A | 12/1990 | Dombrowski et al. ....... 604/198 |
| 5,009,642 A | 4/1991 | Sahi ............................. 604/158 |
| 5,030,208 A | 7/1991 | Novacek et al. ............ 604/195 |
| 5,098,402 A | 3/1992 | Davis ......................... 604/195 |
| 5,104,381 A | 4/1992 | Gresl et al. ................. 604/164 |
| 5,104,382 A | 4/1992 | Brinkerhoff et al. ........ 604/165 |
| 5,139,485 A | 8/1992 | Smith et al. ................ 604/158 |
| 5,190,050 A | 3/1993 | Nitzsche ..................... 128/772 |
| 5,201,710 A | 4/1993 | Caselli ........................ 604/110 |
| 5,226,426 A | 7/1993 | Yoon ........................... 128/753 |
| 5,256,148 A | 10/1993 | Smith et al. ................ 604/158 |
| 5,330,432 A | 7/1994 | Yoon ........................... 604/164 |
| 5,334,159 A | 8/1994 | Turkel ........................ 604/158 |
| 5,336,176 A | 8/1994 | Yoon ........................... 604/51 |
| 5,364,365 A | 11/1994 | Wortrich ..................... 604/158 |
| 5,374,252 A | 12/1994 | Banks et al. ................ 604/158 |
| 5,423,760 A | 6/1995 | Yoon ........................... 604/165 |
| 5,423,770 A | 6/1995 | Yoon ........................... 604/281 |
| 5,476,106 A | 12/1995 | Gartz .......................... 128/898 |
| 5,478,317 A | 12/1995 | Yoon ........................... 604/165 |
| 5,549,564 A | 8/1996 | Yoon ........................... 604/165 |
| 5,562,629 A | 10/1996 | Haughton et al. .......... 604/158 |
| 5,586,991 A | 12/1996 | Yoon ........................... 606/185 |
| 5,634,934 A | 6/1997 | Yoon ........................... 606/185 |
| 5,645,556 A | 7/1997 | Yoon ........................... 606/185 |
| 5,665,072 A | 9/1997 | Yoon ........................... 604/164 |
| 5,718,239 A | 2/1998 | Newby et al. .............. 128/763 |
| 5,779,680 A | 7/1998 | Yoon ........................... 604/164 |
| 5,921,964 A * | 7/1999 | Martin ........................ 604/198 |

* cited by examiner

Primary Examiner—Loan H. Thanh
Assistant Examiner—Catherine S. Williams

(57) ABSTRACT

A blood collector system utilizes a standard disposable needle assembly and standard blood collecting and receiving tubes of the type sealed by a pierceable septum. The system has a hollow cylinder, including an internally apertured sleeve into which the needle assembly is mounted and into which the sealed blood collecting tubes are inserted to be pierced by a needle of the needle assembly. A protective sheath with two clips is concentrically mounted to the barrel cylinder with slot on both sides of the barrel so that the hollow cylinder can move down to cover the patent contacted needle. On both side of the barrel, there are one upper slot and one lower slot, a slot channel between the upper slot and lower slot. The clip is shaped so that it can be snap in the upper and lower slot and can be only slide down from the upper slot to lower slot, but not backwards. After the needle is taken out from a patient, the clip will be pushed down out of the upper slot, then slide down through the slot channel, then be pushed down to snap in the low slot of the barrel in order to cover the used needle from a patient. The apparatus of the invention eliminates the health care worker's exposure to accidental needle pricks.

11 Claims, 12 Drawing Sheets

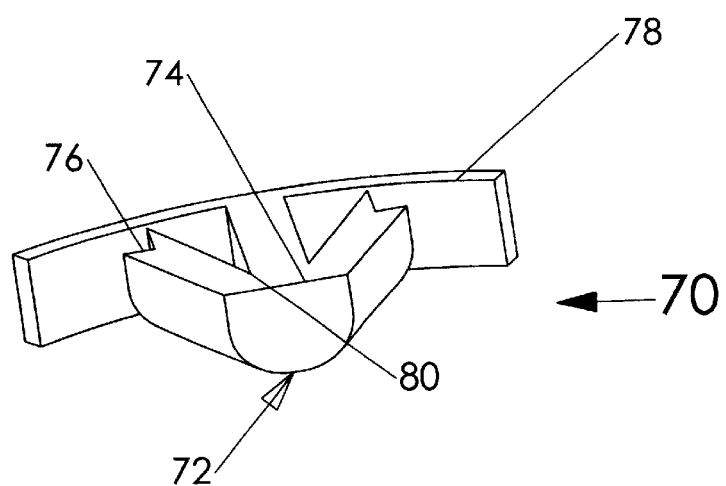
FIG. 9
FIG. 10
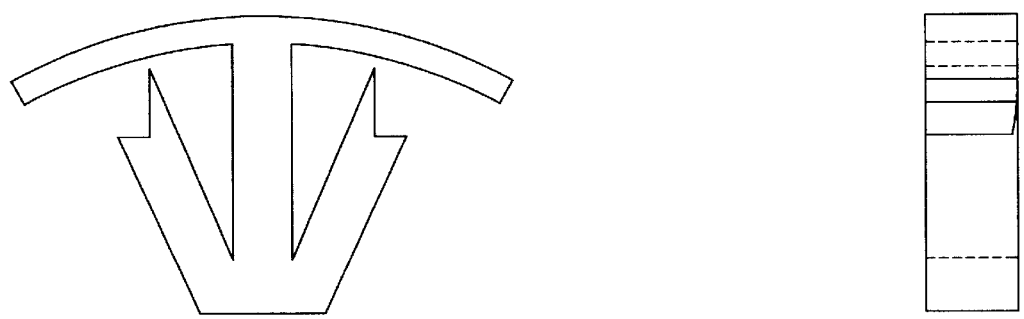
FIG. 11
FIG. 12

SAFETY BLOOD COLLECTOR DEVICE

BACKGROUND OF THE INVENTION

1. Field of the Invention

The present invention is directed to an improved blood specimen collection system for collecting blood from humans and domestic animals. More particularly, the present invention is directed to a blood specimen collector cylinder which includes a protective sheath for covering the needle used during the collection, whereby the used needle can be covered by the protective sheath and discarded without being touched by human hands.

2. Brief Description of the Prior Art

Blood specimen collectors have been known in the art for a long time. More particularly, hypodermic syringes and needles have been used in the art for a long time to draw blood samples from humans and domestic animals. Current hospital and clinical practice, however, requires the taking of blood specimens to occur rapidly and with inexpensive and readily disposable equipment with safety. Ordinary hypodermic syringe and needle combinations do not meet these requirements well. The below-described state-of-the-art blood collecting system, on the other hand, permits rapid and safe collection of blood specimen and uses a disposable blood collector and a collection tube in which the collected blood specimen is initially received and in which it may be stored until desired blood tests are performed. More particularly, and still with reference to the state-of-the-art blood collecting system, for the drawing of blood specimen, a standard disposable needle assembly is placed into a threaded hole in the end wall of a hollow cylinder.

The standard disposable needle assembly includes an externally extending hollow needle which is used to "stick" the patient to draw blood, and another needle extending inwardly into the interior of the hollow cylinder. The two needles are coaxial and are in fluid communication with one another. The collection tube is sealed at one end with a pierceable rubber or like septum. The collection tube is placed within the interior of the cylinder so that the septum is pierced by the inwardly extending needle. The patient's blood is then drawn into the collection tube through the needles without coming into contact with the hollow cylinder. After the collection tube is withdrawn from the cylinder, the blood collection assembly is discarded. For safety reasons this requires placement of a protective cap or sheath on the externally extending needle to avoid accidental needle stick. Although the above-summarized prior art blood specimen collecting apparatus works well, it has a Serious disadvantage in that it is necessary to manipulate and touch the needle assembly after the needle has been in contact with the patient's blood. Such manipulation unfortunately gives rise to the possibility of accidental wounding or pricking of a health care worker by the needle which has been used to collect blood capable of transmitting infectious diseases. It is well known in the art that certain serious, even fatal, diseases, such as hepatitis and AIDS, may be spread in this manner, that is, through accidental contact with infected blood. In light of the foregoing, there is a definite need in the art for a blood sample collecting system or apparatus in which exposure to contaminated needles is minimized or eliminated. This need has not been met in the prior art, although various devices have been made in the hypodermic syringe and related arts for drawing blood specimens and for performing and facilitating the process of injection of drugs with hypodermic syringes. U.S. Pat. No. 3,706,306 describes a blood specimen collecting apparatus substantially of the type which is referred to in the foregoing brief description as "state-of-the-art". U.S. Pat. No. 2,393,196 describes a hypodermic syringe apparatus having a pivotable end piece to which a needle can be mounted. U.S. Pat. Nos. 4,653,511; 4,710,170; 4,123,091; 2,376,436; 4,641,663; French Patent No. 334,207; German Offenlegungsschrift Pat. No. 2451398 and German Offenlegungsschrift Pat. No. 2815377 describe still further blood specimen collector and syringe type devices which comprise the background of the present invention.

SUMMARY OF THE INVENTION

It is an object of the present invention to provide a blood specimen collecting system in which a used needle assembly can be discarded without being touched by human hands, thereby minimizing the health care worker's exposure to contaminated needles which may potentially spread dangerous or fatal diseases. It is another object of the present invention to provide a blood specimen collecting system which meets the above-noted objective and which utilizes standard needle assemblies and blood sample collection tubes. The foregoing and other objects and advantages are attained by a blood collecting system which utilizes standard blood collecting tubes having one of their ends sealed by a pierceable septum. A standard disposable needle assembly used in conjunction with the system includes coaxial first and second hollow needles in fluid communication with one another and an intermediate portion of enlarged diameter which is dimensioned to fit within an aperture provided in an end wall of a hollow cylinder. When the needle assembly is mounted into the cylinder, the first needle is axially extended and available to prick a patient to draw blood. The second needle is extended inwardly to pierce the septum of the standard blood collecting tube which is placed within the interior of the cylinder.

A protective sheath with two clips is concentrically mounted to the barrel cylinder with slot on both sides of the barrel so that the hollow cylinder can move down to cover the patent contacted needle. On both side of the barrel, there are one upper slot and one lower slot, a slot channel between the upper slot and lower slot. The clip is shaped so that it can be snap in the upper and lower slot, and can be only slide down from the upper slot to lower slot, but not backwards. After the needle is taken out from a patient, the clip will be pushed down out of the upper slot, then slide down through the slot channel, then be pushed down to snap in the low slot of the barrel in order to cover the used needle from a patient. When the clip is snapped in the lower slot, it is permanent locked in. The apparatus of the invention eliminates the health care worker's exposure to accidental needle pricks. The features of the present invention can be best understood, together with further objects and advantages, by reference to the following description, taken in connection with the accompanying drawings.

BRIEF DESCRIPTION OF THE DRAWINGS

FIG. 9 is a perspective view of a embodiment of the clip;

FIG. 10 is a top view of FIG. 9;

FIG. 11 is a front view of FIG. 9;

FIG. 12 is a left view of FIG. 9;

DESCRIPTION OF THE PREFERRED EMBODIMENTS

Figure 1:
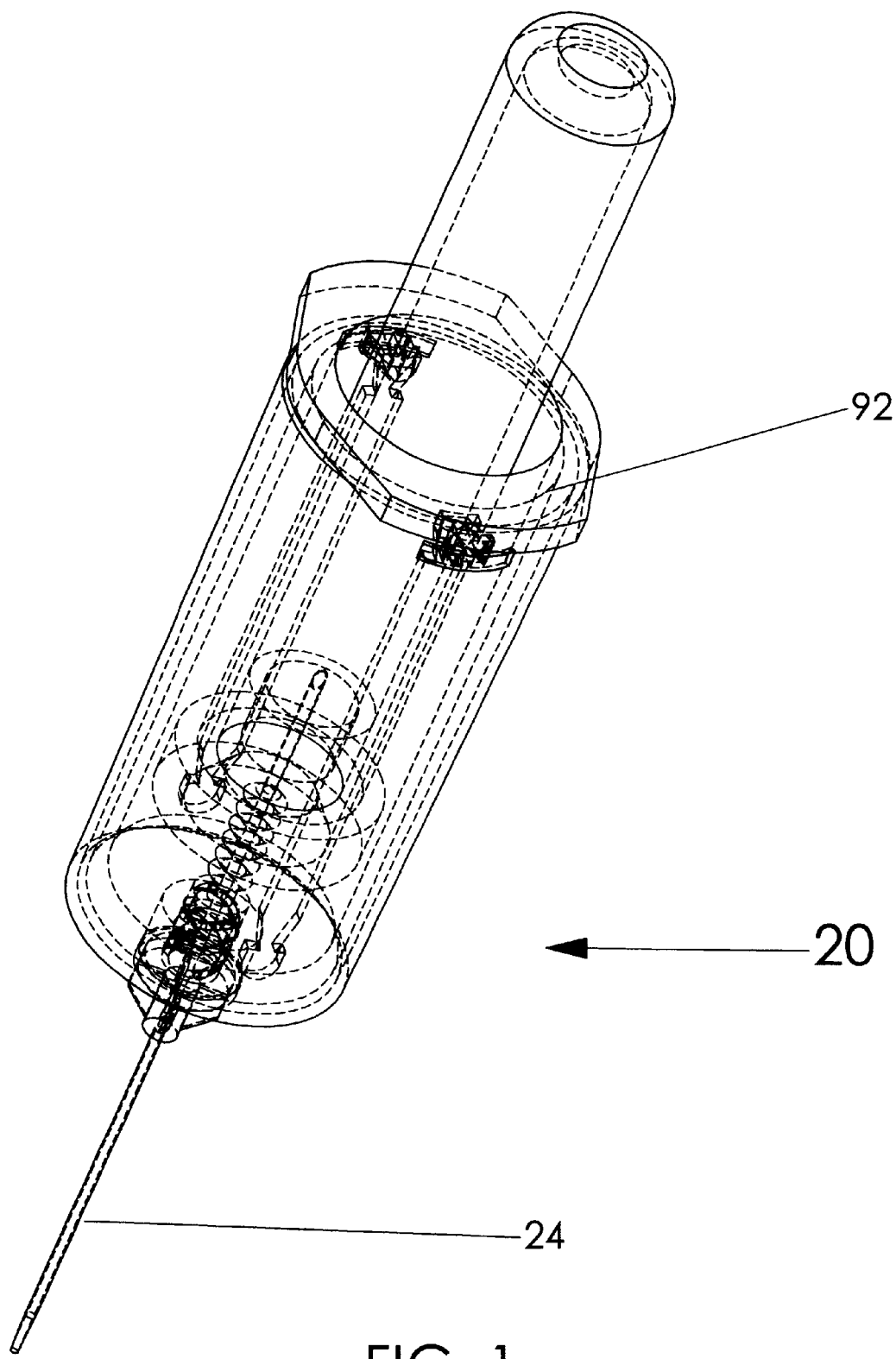
FIG. 1 is a perspective view of a first preferred embodiment of the blood specimen collecting system or apparatus of the present invention.
Figures 2, 3:
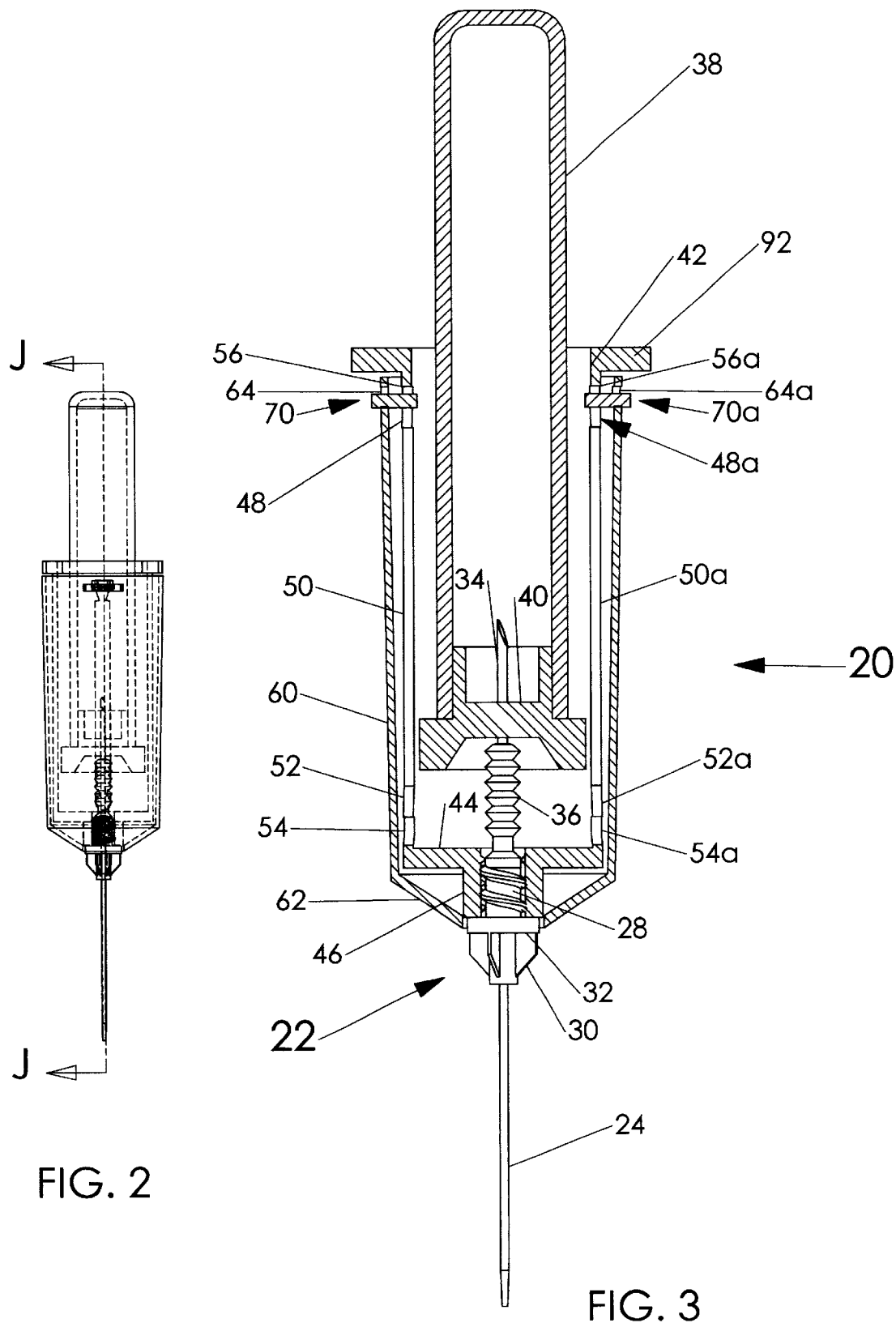
FIG. 2 is a front view of the first preferred embodiment.
FIG. 3 is a cross-sectional view, the cross-section being taken on lines J-J of FIG. 2.

The following specification taken in conjunction with the drawings set forth the preferred embodiments of the present invention. The embodiments of the invention disclosed herein are the best modes contemplated by the inventor for carrying out his invention in a commercial environment, although it should be understood that various modifications can be accomplished within the parameters of the present invention. Knowing to FIGS. Referring. 1 through 6 of the appended drawings, a first preferred embodiment 20 of the blood specimen collector of the present invention is disclosed. It should be noted at the outset that the blood collector of the present invention is designed and adapted to utilize standard disposable needle assemblies and standard blood collection tubes, both of which are ordinarily used in the art for the collection of blood specimens. Although these standard items do not, in and of themselves, comprise the present invention, they are described here first, to the extent necessary to explain and illuminate the present invention. Thus, a standard needle assembly 22 includes a first needle 24 which is normally used to penetrate a patient's veins (or other parts of the patient's body) to draw blood.

An intermediate portion of the needle assembly 22 is a plastic body 26 of larger diameter than the first needle 24. The plastic body 26 is substantially cylindrical, and has a threaded part 28 and a ribbed part 30, with the two being separated from each other by a radically extending shoulder 32. A second needle 34 extends from the plastic body 26 in a direction which is opposite to that of the first needle 24.

Figures 4, 5:
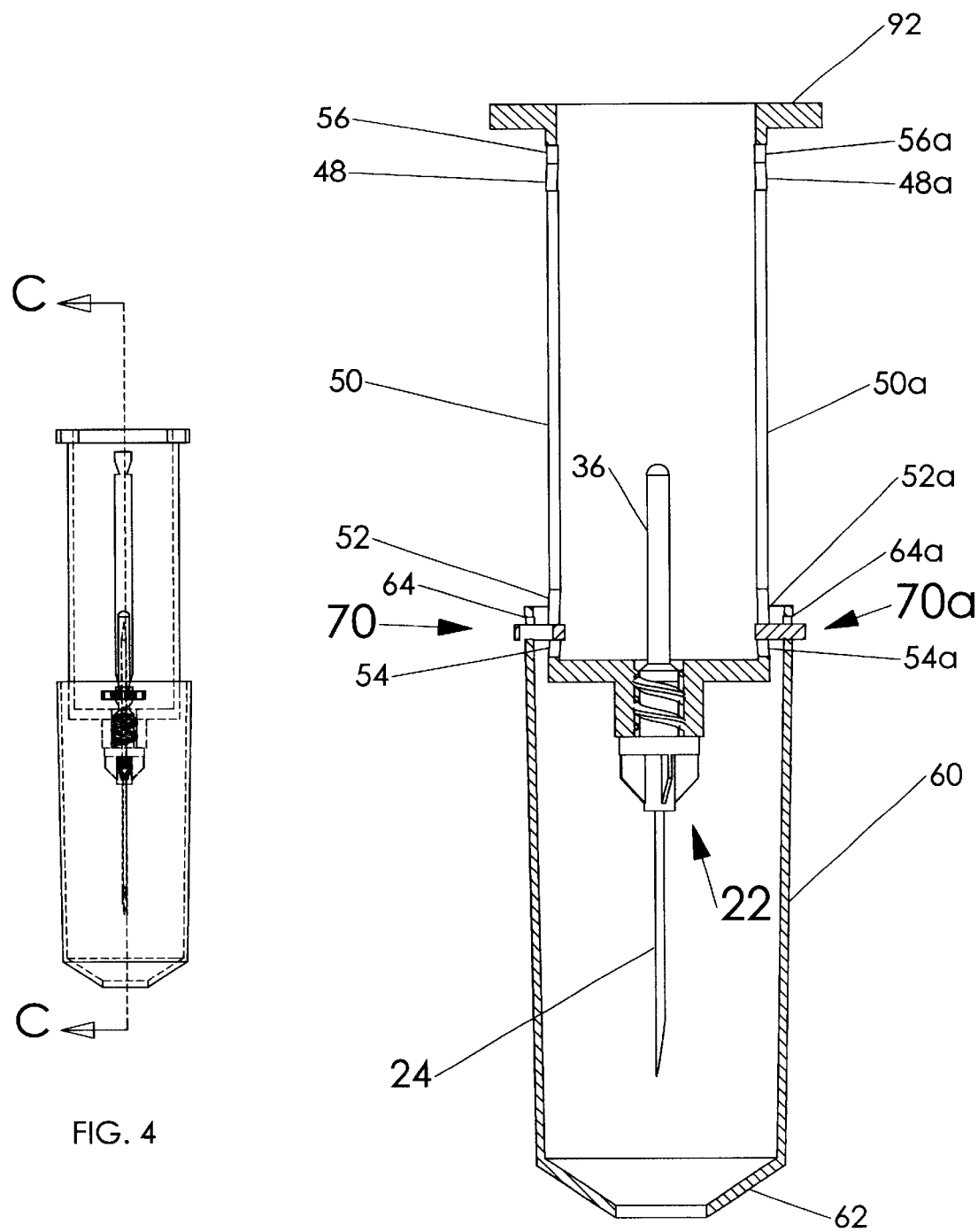
FIG. 4 is a front view of the blood specimen collecting system or apparatus of the present invention after blood collection.
FIG. 5 is still another cross-sectional view, analogous to the cross-sectional view taken on lines C-C of FIG. 4, but showing a needle assembly in a sheath and in a hollow cylinder of the blood specimen collecting system of the present invention.

The two needles 24 and 34 are hollow and in fluid communication with one another. In fact, for practical construction of the needle assembly 22, the two needles 24 and 34 comprise the same piece of metal to which the plastic body 26 is attached. Still in accordance with standard practice in the art, the needle assembly 22 is usually packaged and stored in protective sheaths (not shown) which are separately removable from the first and second needles 24 and 34, respectively. Moreover, the second needle 34 usually carries a protective rubber or like sleeve 36 which may be retracted on the second needle 34, as is shown on FIG. 5. The blood collection tubes 38 used in the present invention comprise tubular receptacles of glass or plastic, which have a resilient septum seal 40 penetrable by the second needle 34. The interior of the blood collection tube 38 is usually evacuated so as to contain partial vacuum. As it will be readily understood by those skilled in the art, the vacuum in the blood collection tube 38 eliminates the need for an air vent or vented needle during the blood collection process. The appended drawing FIGURES show a tubular, hollow cylinder inside wall 42 having a front wall 44 which includes a relatively short sleeve 46. Prior to taking of blood specimens the threaded portion 28 of the plastic body 26 is fitted into the sleeve 46, whereby the needle assembly 22 is mounted to the hollow cylinder 100. The blood collection tube 38 is placed and pushed into the hollow cylinder inside wall 42 so that the second needle 34 penetrates the seal 40, as is specifically shown on FIG. 5. As it will be readily understood by those skilled in the art, under the above-described circumstances blood can be drawn from a patient's body into the blood collection tube 38. After the first needle 24 is withdrawn from the patient's body, and the blood collection tube 38 is removed from the cylinder 42, the collected blood specimen can be stored in the collection tube 38. The needle assembly 22 which has come into contact with the patient's blood, must be discarded. The hereinafter-described novel features of the present invention facilitate the step of discarding the used needle assembly 22, and render it much less likely that a doctor, nurse, or other health care worker accidentally should prick or injure himself or herself with the used needle.

Figure 6:
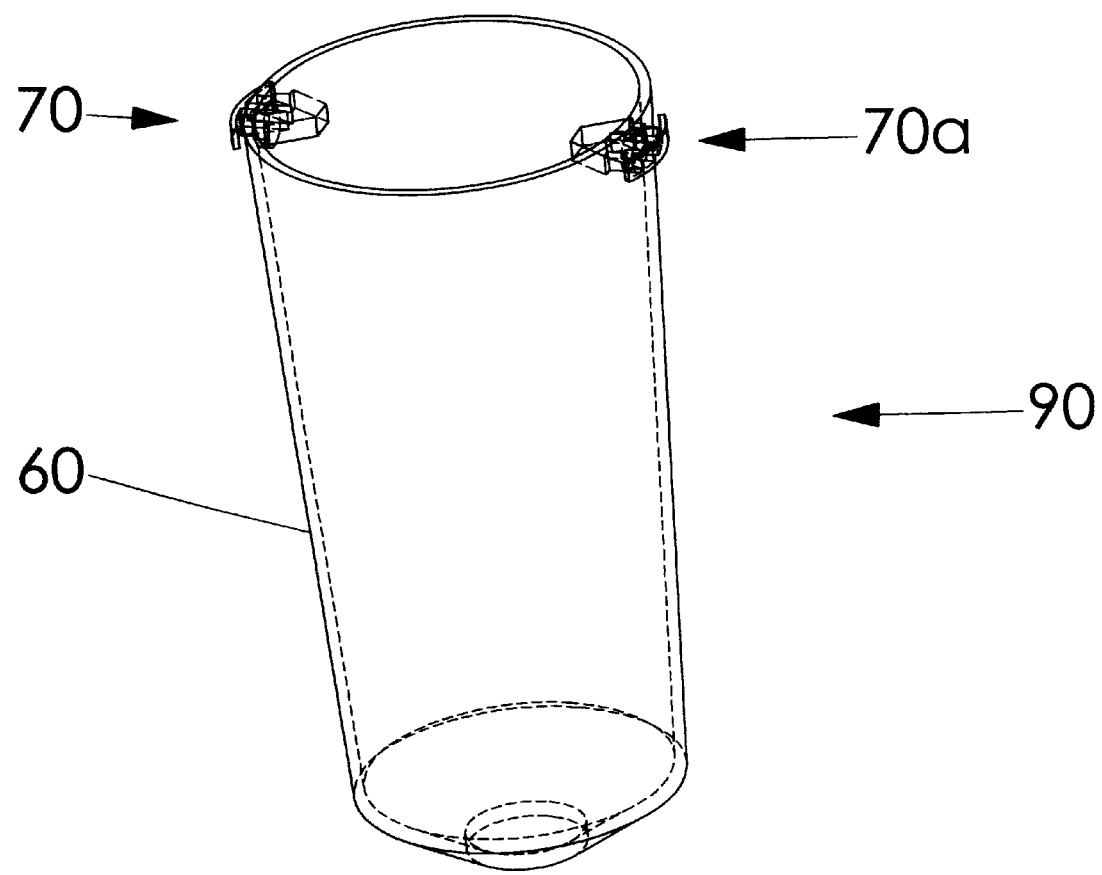
FIG. 6 is a perspective view of a embodiment of the slide sheath.
Figure 7:
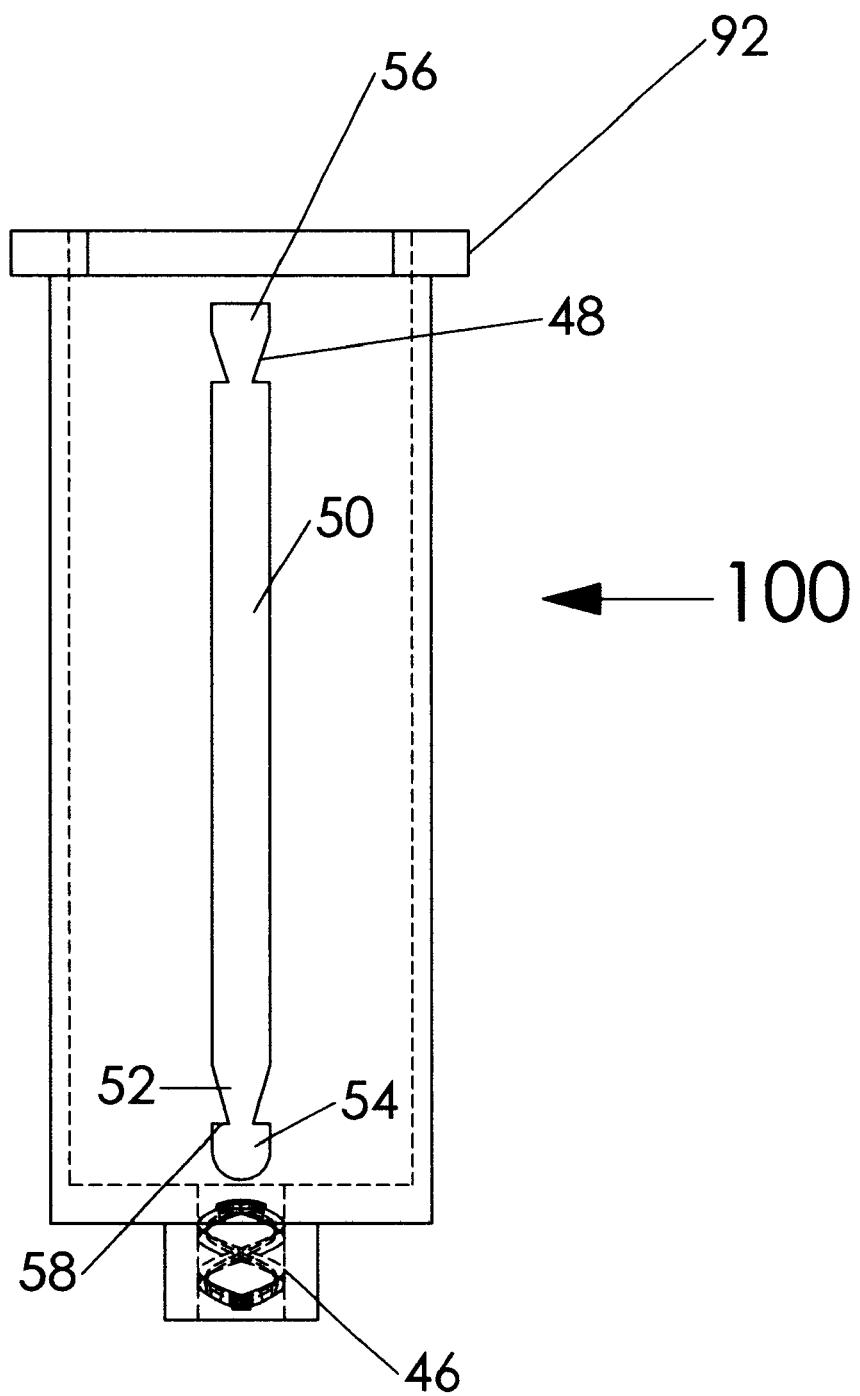
FIG. 7 is a front view of the hollow cylinder.
Figure 8:
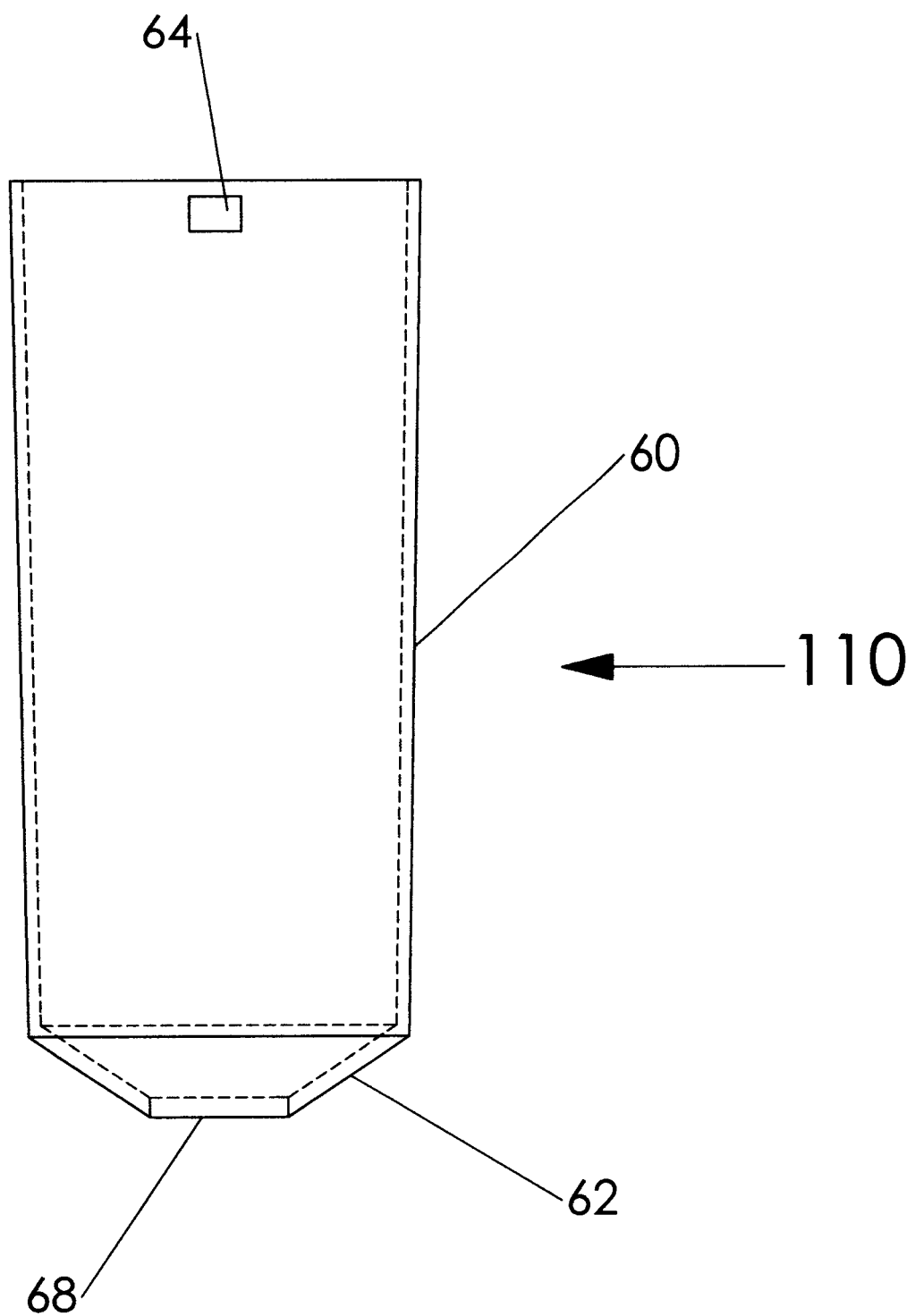
FIG. 8 is a front view of the sheath.
Figure 13:
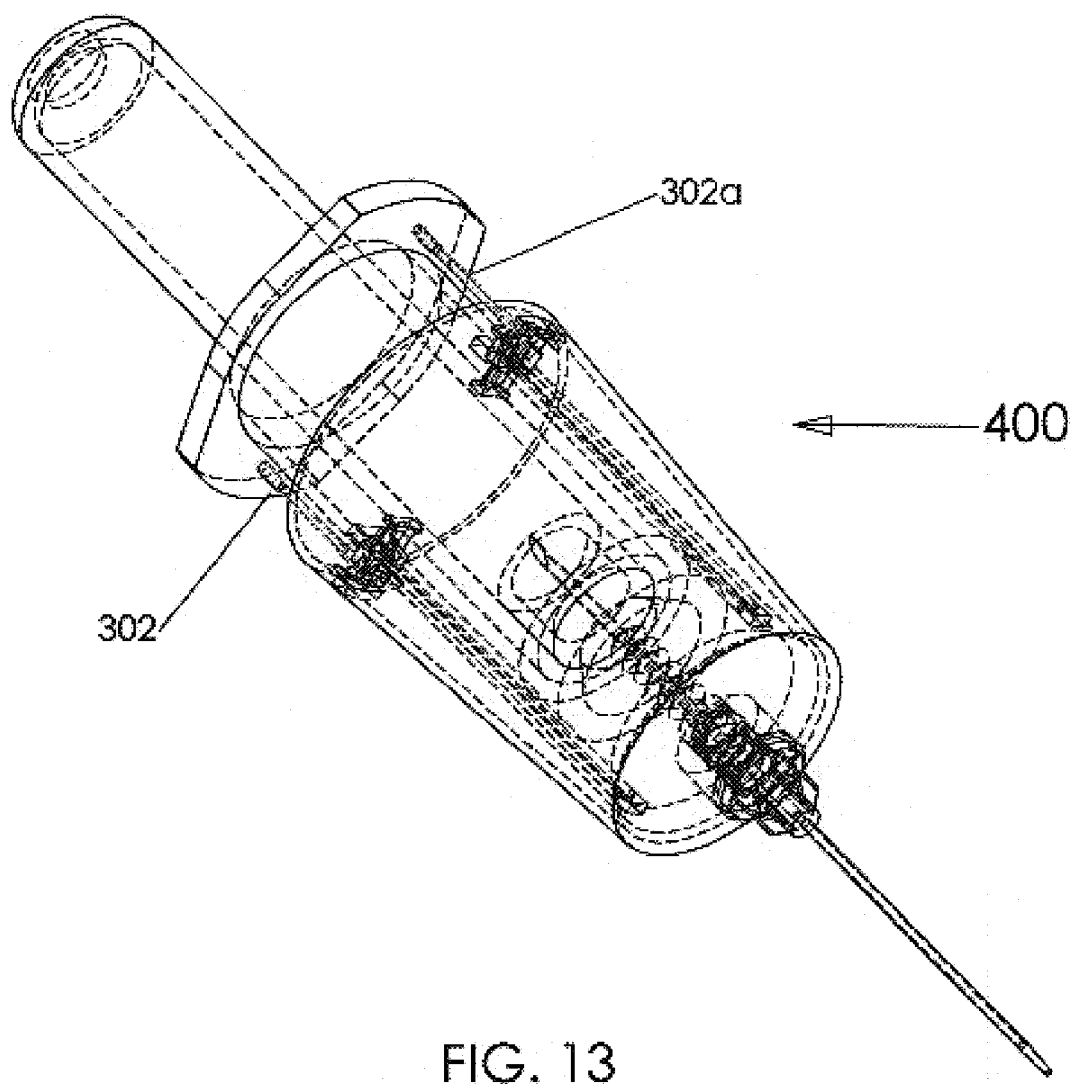
FIG. 13 is a perspective view of a first preferred embodiment of the safety spring activated blood specimen collecting system or apparatus of the present invention.
Figure 14:
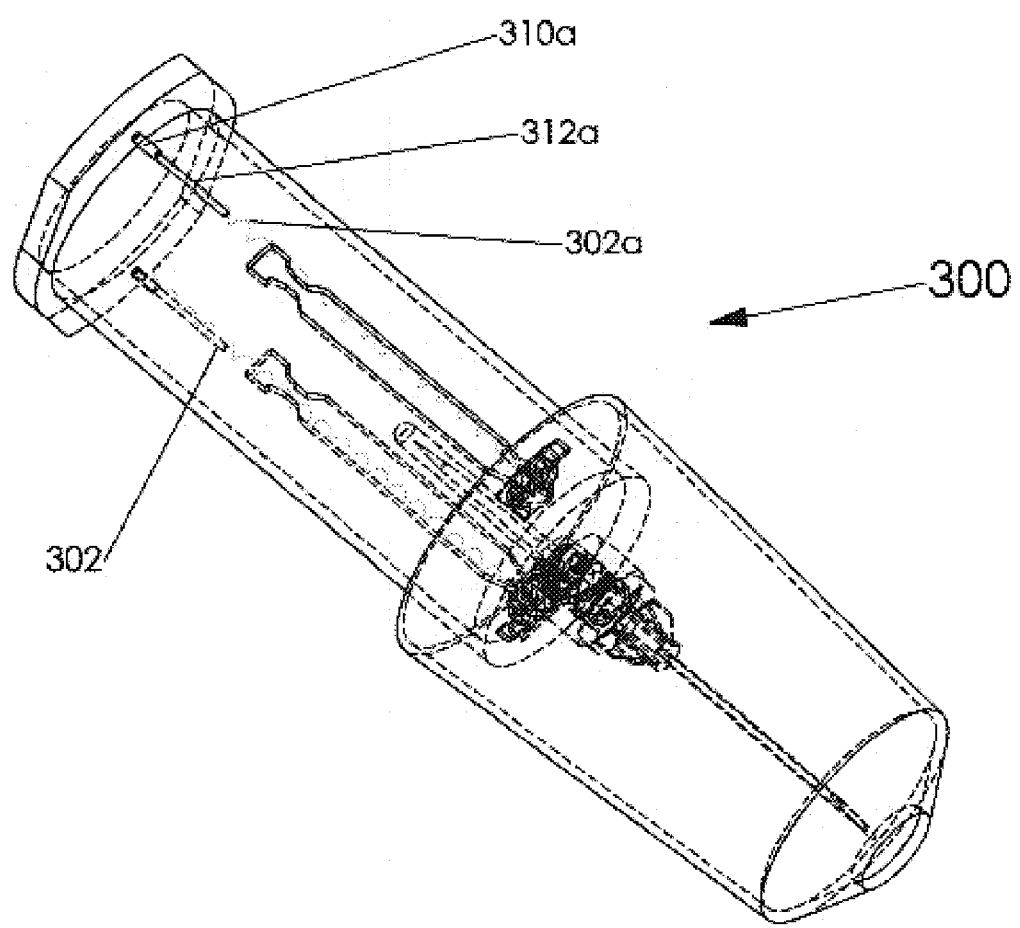
FIG. 14 is a perspective view of a first preferred embodiment of the safety spring activated blood specimen collecting system or apparatus of the present invention after blood collection.
Figures 15, 16:
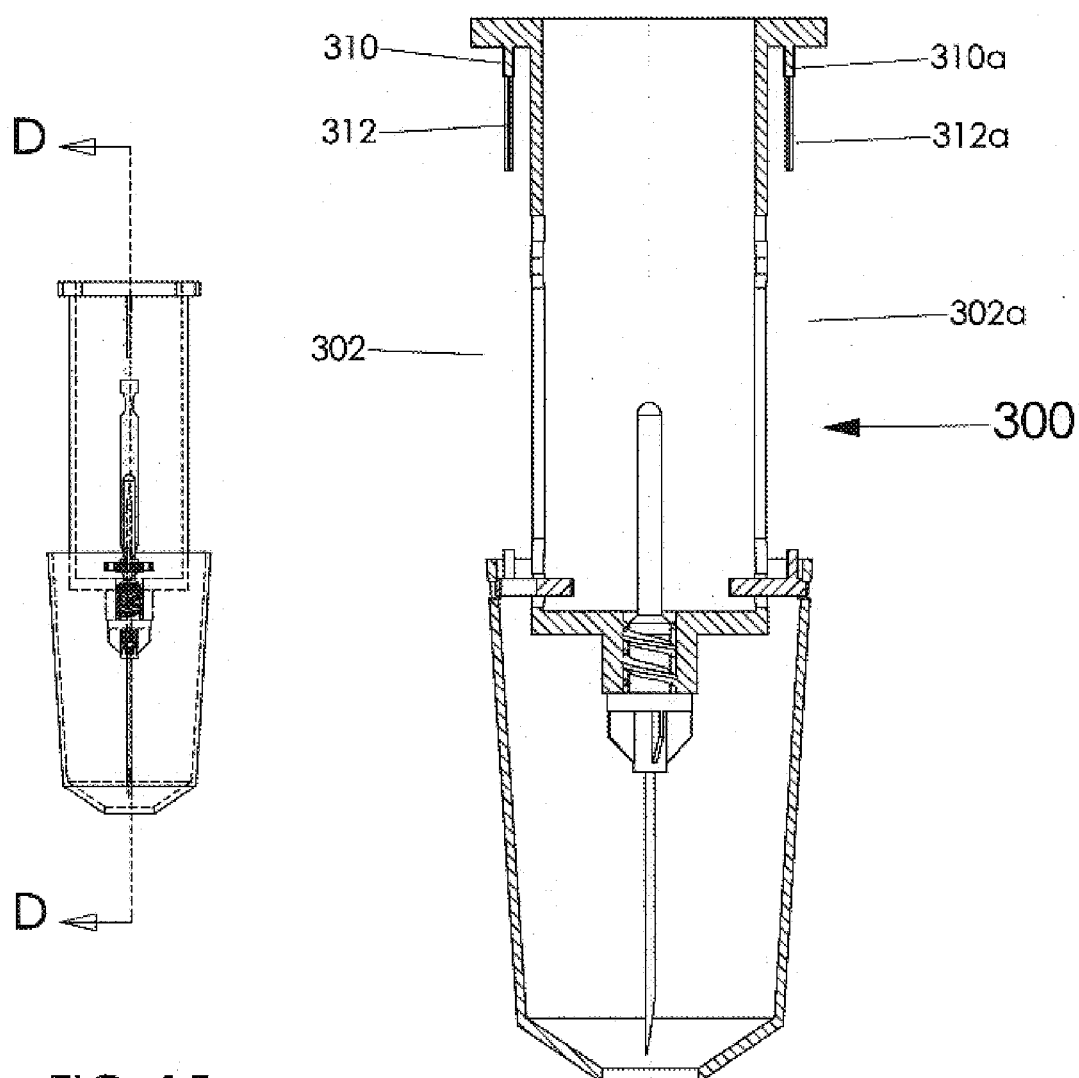
FIG. 15 is a front view of the safety spring activated blood specimen collecting system or apparatus of the present invention after blood collection.
FIG. 16 is still cross-sectional view taken on lines D-D of FIG. 15, but showing a needle assembly in a sheath and in a hollow cylinder of the safety spring activated blood specimen collecting system of the present invention.
Figure 17:
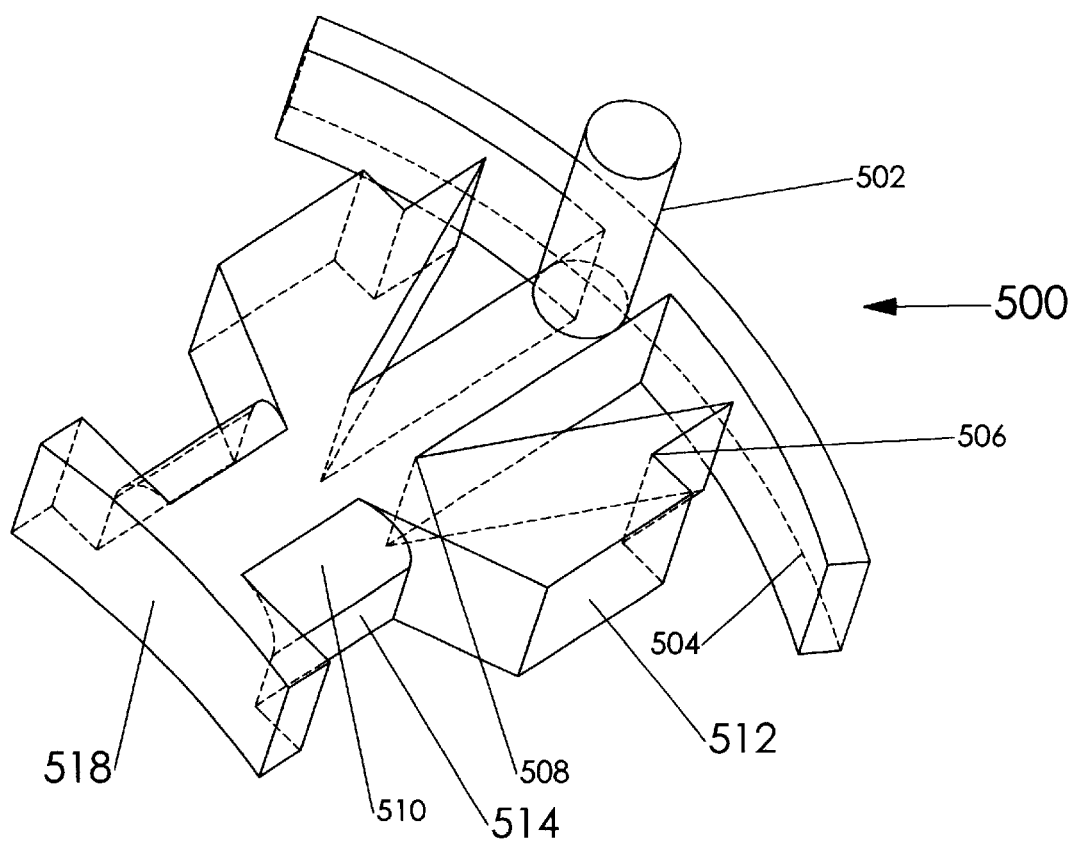
FIG. 17 is a perspective view of a embodiment of the clip for the safety spring activated blood specimen collecting system.
Figure 18:
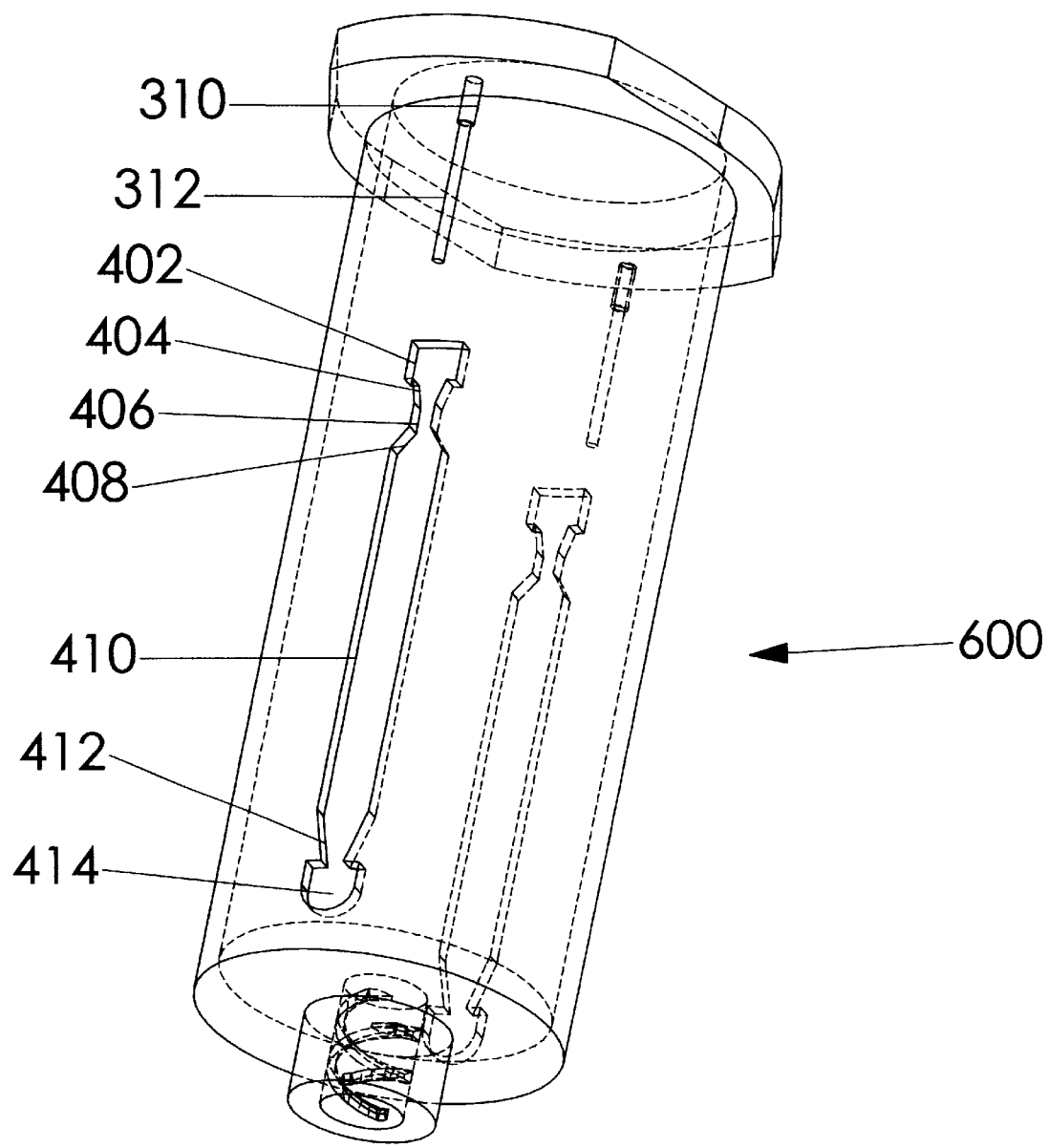
FIG. 18 is a perspective view of a embodiment of the hollow cylinder for the safety spring activated blood specimen collecting system.

The embodiment of the clip 70 is snapped in the sheath hole 64 as shown in FIG. 6. Before use, the clip 70 assembled with the sheath 110 is snapped in the upper slot 56 of the hollow cylinder. After injection from a patient, the slide sheath 90 can be pushed down by holding the finger flange 92 of the hollow cylinder 100 and the outside wall 60 of the slide sheath 90. The lower curve edge 72 of the clip will be slid down through the upper reducer 48 of the hollow cylinder 100. Then, the clip 70 is easily slid down the slot channel 50 of the hollow cylinder 100. After that, the clip 70 is pushed down into the lower slot 54 of the hollow cylinder 100 through the lower reducer 52 of the hollow cylinder 100. The straight edge 76 of the clip 70 is against the upper straight face 58 of the lower slot 54 so that the slide sheath is permanently locked in the lower slot 54 without the possibility of being slid backwards as shown in FIG. 7 and FIG. 9. In an alternative way, the slide sheath 90 in FIG. 6 can be pushed down by two compression springs 302, 302a as shown in FIG. 14. The protect sheath 110 is made of semi-rigid material so that it can be deformed to an oval shape by squeeze as shown in FIG. 8. The embodiment of the alternative invention is shown from FIG. 13 to FIG. 18. Before use, the clip 500 is snapped in the upper slot 402 of the hollow cylinder 600. After collecting blood from a patient or a animas, a health worker can squeeze the protect sheath 110 so that the wider part 512 of the clip 500 can be out of the upper slot 402 of the hollow cylinder 600 and the narrow part 514 of the clip 500 will be pushed down by the compression spring 302 through the channel slot 410 to the lower slot 414 permanently locked. The end shaft 502 of the clip 500 and the shaft 312 at the finger flange 405 of the hollow cylinder 600 are used to guide a compression spring. 404 and 412 are reducers. The end cover 518 of the clip is used to permanently lock the clip 500 at the lower slot 414 of the hollow cylinder 600 as shown in FIG. 17 and FIG. 18.

What is claimed is:

1. A blood specimen collecting system comprising:

a blood draw holder in the shape of hollow cylinder having on opposite sides of the holder an upper slot, a lower slot and a slot channel and having an apertured sleeve with a screw surface in an end wall adapted to receive a needle assembly, the hollow cylinder adapted to receive a blood sample collector tube at least partially within a hollow interior of the holder, the collector tube being sealed at one of its ends by a septum pierceable with a needle;

a needle assembly having an intermediate portion which is dimensioned to fit and be mounted in the screw surface of the holder, a first hollow needle portion extending axially outwardly from the holder, and a second hollow needle portion extending axially inwardly into the interior of the cylinder, the first and second hollow needle portions being in fluid communication with one another, the first hollow needle portion being adapted to pierce a vein, and the second hollow needle portion being adapted to pierce the septum; and a protective sheath concentrically mounted to the holder, the sheath having two holes on opposite sides, each hole having a clip snapped in, the clips having a lower curved edge and an upper straight edge, wherein the clips slide to the lower slots of the holder through the slot channels to cover the needle with the sheath after use, and wherein the clips are locked in the lower slots of the holder.

2. The blood specimen collecting system of claim 1 wherein the intermediate portion of the needle assembly is threaded, and wherein the screw surface of the apertured sleeve in the end wall of the holder has at least one interior thread complementary to the thread of the intermediate portion.

3. The blood specimen collecting system of claim 1 wherein the upper and lower slots of the holder are connected to the slot channels with reducers.

4. The blood specimen collecting system of claim 1 further comprising a reducer between the upper slots and the slot channels so that the clips need to be pushed into the slot channels.

5. The blood specimen collecting system of claim 1 further comprising a second reducer between the slot channels and the lower slots so that the clips need to be pushed into the lower slots from the slot channels and the clips will be permanently locked in the lower slots of the holder.

6. The blood specimen collecting system of claim 1 wherein the holder, the sheath and the clips are entirely made of plastic material.

7. The blood specimen collecting system of claim 1 wherein a health worker can squeeze the sheath after collecting blood from a patient or an animal so that the wide width of the clips can move out of the upper slots of the holder and the narrow width of the clips will be pushed by two compression springs connected on two sides of the holder through the channel slots to the lower slots.

8. The blood specimen collecting system of claim 1 further comprising the clips having a wide part and narrow part, and on one side of the clip there is a guide shaft which guides a compression spring.

9. The blood specimen collecting system of claim 1 further comprising a guide shaft on both side of a finger flange of the holder.

10. The blood specimen collecting system of claim 1 wherein the clips have a narrow width and a wide width to prevent movement of the clips out of the slots and the slot channels.

11. The blood specimen collecting of claim 10 wherein the narrow width of the clip fits in the slots of the holder and slides through the slot channel, and the wide width of the clip is used to prevent the clip from displacement out of the slots and the slot channel.

* * * * *